United States Patent [19]

Cummins

[11] Patent Number: 4,820,514
[45] Date of Patent: Apr. 11, 1989

[54] LOW DOSAGE OF INTERFERON TO ENHANCE VACCINE EFFICIENCY

[75] Inventor: Joseph M. Cummins, Amarillo, Tex.

[73] Assignee: Texas A&M University System, College Station, Tex.

[21] Appl. No.: 814,317

[22] Filed: Dec. 30, 1985

[51] Int. Cl.$^4$ .............................................. A61K 45/02
[52] U.S. Cl. .................................... 424/85.4; 435/811
[58] Field of Search ....................... 424/85, 88, 92, 87, 424/93

[56] References Cited

U.S. PATENT DOCUMENTS

| | | | |
|---|---|---|---|
| 3,906,092 | 9/1975 | Hilleman et al. | 424/85 |
| 4,053,582 | 10/1977 | Stickl | 424/85 |
| 4,273,703 | 6/1981 | Osther et al. | 424/85 |
| 4,322,404 | 3/1982 | Gaure et al. | 424/89 |
| 4,429,045 | 1/1984 | Bass et al. | 435/235 |
| 4,460,574 | 7/1984 | Yabrov | 424/85 |
| 4,462,985 | 7/1984 | Cummins, Jr. | 424/85 |
| 4,497,795 | 5/1985 | Cummins | 424/85 |
| 4,675,184 | 6/1987 | Hasegawa et al. | 424/85 |

FOREIGN PATENT DOCUMENTS

| | | |
|---|---|---|
| 0180737 | 5/1986 | Fed. Rep. of Germany . |
| PCT/US81/-01103 | 8/1981 | World Int. Prop. O. . |

OTHER PUBLICATIONS

Epstein, L., Interferons and Their Actions, CRC Press, Inc., Boca Raton, Florida, Stewart II et al. editors, pp. 102–104, 1977.
Sonnenfeld et al., Cellular Immunology, vol. 40, pp. 285–293, 1978.
Rodder, H., Thumann, D., Thumann, E., *Tierarztliche Umschau*, vol. 34, No. 10, 1979, pp. 720–724 (summary).
Toneva, V., *Bulletin de l'Office International des Epizooties*, vol. 88, 1977, pp. 631–637 (Summary).
"In Vivo and Clinical Studies", Norman B. Finter & Robert K. Oldham, eds., Interferon, vol. 4, 1985, pp. 137, 148, 173, 218, 226, 284, 285, 330.
*Chemical Abstracts*, vol. 67, 1967, p. 7536 [80070u], Litvinov, A. N.
"Time and Dosage Dependence of Immunoenhancement by Murine Type II Interferon Preparations", Cellular Immunology, 40, 1978, pp. 285–293.
"Antiviral Effect of Bacterially Produced Human Interferon (Hu-IFNa$_2$) Against Experimental Vaccinia Infection in Calves", Journal of Interferon Research, 5:129–136, 1985, Werenne, J., Broecke, C. V., Schwers, A., Goossens, A., Bugyaki, L., et al.
"Effect of Human Leukocyte A Interferon on Prevention of Infectious Bovine Rhinotracheitis Virus Infection of Cattle", Roney, C. S. et al., *Am J. Vet. Res.*, vol. 46, No. 6, Jun. 1985, pp. 1251–1255.
"Response of Feline Leukemia Virus-induced Nonregenerative Anemia to Oral Administration of an Interferon-containing Preparation", Feline Practice, vol. 12, No. 3, May–Jun. 1982, pp. 6–15, Tompkins, M. B. and Cummins, J. M.
"Interferon Enters The Fray", *Farm Journal*, Oct. 1985, pp. 12–13, Miller, B.
"Interferon as an Adjuvant for Hepatitis B Vaccination in Non- and Low-Responder Populations", Grob, P. J. et al., *Eur. J. Clin. Microbiol.*, Jun. 1984, vol. 3, No. 3, pp. 195–198.
"Protection of Calves Against Rhinovirus Infection by Nasal Secretion Interferon Induced by Infectious Bovine Rhinotracheitis Virus", *American Journal of Veterinary Research*, Cummins, J. M. and Rosenquist, B. D., Feb. 1980, vol. 41, No. 2, pp. 161–165.
"Bovine Respiratory Disease-A Symposium", R. W. Loan, ed., Texas A&M University Press, College Station, TX, 1984, pp. 484–485.
"Activity Of Exogenous Interferon In The Human Nasal Mucosa", Texas Reports on Biology and Medicine, vol. 35, 1977, Greenberg, S. B., Harmon, M. W. and Johnson, P. E., pp. 491–496.
"Inhibition of Respiratory Virus Infection by Locally Applied Interferon", Merigan, T. C., Hall, T. S., Reed, S. E., and Tyrrell, D. A., *The Lancet*, Mar. 17, 1973, pp. 563–567.
"Trials of Interferon in Respiratory Infections of Man", Tyrrell, D. A. J., *Texas Reports on Biology and Medicine*, vol. 35, 1977, pp. 486–490.
"Bacteria-Derived Human Leukocyte Interferons After in Vitro Humoral and Cellular Immune Responses", Cellular Immunology, 82, 1983, pp. 269–281, by Shalaby, M. R. and Weck, P. K.
"Clinical and Laboratory Investigations on Man: Systemic Administration of Potent Interferon to Man", *J. Natl. Cancer Inst.*, 51: 733–742, 1973, by Strander, H., Cantell, K., Carlstrom, G. and Jakobsson, P. A.
"Application of Human Leukocyte Interferon in Severe Cases of Virus B Hepatitis", Vlatkovic, R., et al., *Proc. Symposium on Interferon 1979*, Yugoslav Academy of Sciences and Arts, Zagreb, pp. 173–183.
"Effect of Interferon on Vaccination in Volunteers", *The Lancet*, Apr. 28, 1962, pp. 873–875 (Report to Medical Research Council from the Scientific Committee on Interferon).
"Induction of Ocular Resistance to Vaccinia Virus by Typhoid Vaccine: Role of Interferon", Oh, J. O. and Yoneda, C., *The Journal of Immunology*, vol. 102, No. 1, 1969, pp. 145–154.

(List continued on next page.)

*Primary Examiner*—Blondel Hazel

[57] ABSTRACT

A biologically active interferon can be administered to an animal in conjunction with the administration of a vaccine to improve the vaccine efficiency and allow the use of a smaller vaccination dose. This procedure will cause a less severe vaccine infection in the animal than if no interferon was administered.

7 Claims, No Drawings

OTHER PUBLICATIONS

"Clinical Trials with Exogenous Interferon: Summary of a Meeting", *The Journal of Infectious Diseases,* vol. 139, No. 1, Jan. 1979, pp. 109-123.

"Some Results and Prospects in the Study of Endogenous and Exogenous Interferon", *The Interferson, An International Symposium,* Soloviev, V. D., Geo. Rita, ed., Academic Press, 1968, pp. 233-243.

"Influenza and Interferon Research in the Soviet Union-Jan. 1973", *The Journal of Infectious Diseases,* vol. 128, No. 2, Aug. 1973, pp. 261-264.

"The Results of Controlled Observations on the Prophylaxis of Influenza with Interferon", Solov'ev, V. D., *World Health Organization,* 1949, 41, 683-688.

"Children's Respiratory Viral Diseases Treated With Interferon Aerosol", Jia-xiong, D. et al., *Chinese Medical Journal,* 100(2): 162-166, 1987.

*Essential Clinical Virology,* R. G. Sommerville, Blackwell Scientific Publications, pp. 154-157.

"Comparative Intranasal Pharmacokinetics of Interferon Using Two Spray Systems", Davies, H. W. et al., *J. Interferon Research, 1983, pp. 443-449.*

"The Common Cold Control?", Couch, R. B., *The Journal of Infectious Diseases,* vol. 150, No. 2, Aug. 1984, pp. 167-173.

*Principles and Practice of Infectious Diseases,* 2nd. ed., Mandell, G. L., Douglas, R. G. Jr., Bennett, J. E. eds., A Wiley Medical publication, pp. 85-96, 863, 968.

*Antiviral Agents and Viral Diseases of Man,* edited by G. J. Galasso, T. C. Merigan, R. A. Buchanan, Raven Press, New York, 1979, pp. 407-408, 430-431.

*Antiviral Agents and Viral Diseases of Man,* edited by G. J. Galasso, T. C. Merigan, R. a. Buchanan, Raven Press, New York, 1984, pp. 145-178, 344-345.

"Interferon Perspective", Information on Interferon provided in 1981 by the International Preventative Medicine Foundation, Melbourne FL, Ronald Jones, Vice President.

American Interhealth, Melbourne Beach, Florida, Production Information.

Biovet International, Inc., Canine and Feline Interferons, 1981 Product Description and Label.

"Agriferon®-C", Immuno Modulators Laboratories, Inc., Stafford, Texas, Lymphokine Preparation for Prophylactic Treatment of Infectious Bovine Rhinotracheitis Virus Associated with Shipping Fever-for Cattle Use in Texas Only, product brochure.

"Agriferon®-C", A bold new approach to managing shipping fever in cattle, Immuno Modulators Laboratories, Inc., Stafford, Texas, product advertisement.

"Equiferon", a totally new approach to viral respiratory infection in horses, Immuno Modulator Laboratories, Inc., Stafford, Texas, 1985, product advertisement.

"Pet Interferon Alpha", Amarillo Cell Culture Company, Inc., Amarillo, Texas, Lymphokine Preparation For Treatment of Feline Leukemia Virus and Canine Parvovirus Diseases, product brochure.

LOW DOSAGE OF INTERFERON TO ENHANCE VACCINE EFFICIENCY

BACKGROUND OF THE INVENTION

This invention relates generally to methods of enhancing the efficiency of vaccines in warm-blooded vertebrates. The methods involve administering interferon to a warm-blooded vertebrate in conjunction with administration of a vaccine.

"Interferon" is a term generically comprehending a group of vertebrate glycoproteins and proteins which are known to have various biological activities, such as antiviral, antiproliferative, and immunomodulatory activity in the species of animal from which such substances are derived. The following definition for interferon has been accepted by an international committee assembled to devise a system for the orderly nomenclature of interferons: "To qualify as an interferon a factor must be a protein which exerts virus nonspecific, antiviral activity at least in homologous cells through cellular metabolic processes involving synthesis of both RNA annd protein." *Journal of Interferon Research,* 1, pp. vi (1980).

Since the first descriptions of interferon by Isaacs and Lindeman [See, *Proc. Roy. Soc. London (Ser. B)*, Vol. 147, pp. 258 et seq. (1957) and U.S. Pat. No. 3,699,222], interferon has been the subject of intensive research on a worldwide basis. Publications abound concerning the synthesis of interferon; M. Wilkinson and A. G. Morris, Interferon and the Immune System 1: Induction of Interferon by Stimulation of the Immune System, Interferons: From Molecular Biology to Clinical Application, Eds: D. C. Burke and A. G. Morris, Cambridge Univ. Press, 1983, pp. 149-179; P. I. Marcus, Chapter 10, Interferon Induction by Virus, Interferons and Their Applications, Eds: P. E. Came and W. A. Carter, Springer Verlag, (Handbook of Experimental Pharmacology V. 71) 1984, pp. 205-232; its proposed molecular characterizations; P. B. Sehgal, How Many Human Interferons Are There? Interferon 1982, Ed I. Gresser, Academic Press, 1982, pp. 1-22; J. Collins, Structure and Expression of the Human Interferon Genes, Interferons: From Molecular Biology to Clinical Application, Eds: D. C. Burke and A. G. Morris, Cambridge Univ. Press, 1983, pp. 35-65; K. C. Zoon and R. Wetzel, Chapter 5, Comparative Structures of Mammalian Interferons, la: Interferons and Their Applications, Eds: P. E. Came and W. A. Carter, Springer Verlag, (Handbook of Experimental Pharmacology V. 71) 1984, pp. 79-100; its clinical applications; M. Krim, Chapter 1, Interferons and Their Applications: Past, Present, and Future, Interferons and Their Applications, Eds: P. E. Came and W. A. Carter, Springer Verlag, (Handbook of Experimental Pharmacology V. 71) 1984; S. B. Greenberg and M. W. Harmon, Chapter 21, Clinical Use of Interferons: Localized Applications in Viral Diseases, Ibid. pp. 433-453; and proposed mechanisms of its antitumor, antiviral, and immune system activities. G. M. Scott, The Antiviral Effects of Interferon, From Molecular Biology to Clinical Application, Eds: D. C. Burke and A. G. Morris, Cambridge Univ. Press, 1983, pp. 279-311; M. McMahon and I. M. Kerr, The Biochemistry of the Antiviral State, Ibid. pp. 89-108; J. S. Malpas, The Antitumor Effects of Interferon, Ibid. pp. 313-327; J. Taylor-Papadimitrion, The Effects of Interferon on the Growth and Function of Normal and Malignant Cells, Ibid. pp. 109-147.

Because of the intensity and disparate origins of research concerning interferon and its characteristics and uses, there exits a substantial lack of uniformity in such matters as classification of interferon types. There are also numerous, sometimes contradictory, theories concerning the mode of action of interferon in producing clinical effects. The following brief summary of the current state of knowledge regarding interferon will aid in understanding the present invention.

Although originally isolated from cells of avian origin (chick allantoic cells), interferon production has been observed in cells of all classes of vertebrates, including mammals, amphibians, and reptiles. Interferon production by vertebrate cells is seldom spontaneous but is often readily "induced" by treatment of cells (in vivo or in vitro) with a variety of substances including viruses, nucleic acids (including those of viral origin as well as snythetic polynucleotides), lipopolysaccharides, and various antigens and mitogens.

Interferons have generally been named in terms of the species of animal cells producing the substance (e.g., human, murine, or bovine), the type of cell involved (e.g., leukocyte, lymphoblastoid, fibroblast) and, occasionally, the type of inducing material responsible for interferon production (e.g., virus, immune). Interferon has been loosely classified by some researchers according to induction mode as either Type I or Type II, with the former classification comprehending viral and nucleic acid induced interferon and the latter class including the materials produced as a lymphokine through induction by antigens and mitogens. More recently, the international committee devising an orderly nomenclature system for interferon has classified interferon into types on the basis of antigenic specificities. In this newer classification, the designations alpha ($\alpha$), beta ($\beta$), and gamma ($\gamma$) have been used to correspond to previous designations of leukocyte, fibroblast, and type II (immune) interferons, respectively. Alpha and beta interferons are usually acid-stable and correspond to what have been called type I interferons; gamma interferons are usually acid-labile and correspond to what has been called type II interferons. The international committee's nomenclature recommendations apply only to human and murine interferons. *Journal of Interferon Research,* 1 pp. vi (1980).

Determination of precise molecular structures for interferon was for some time beyond the capacities of the art. In the years since interferon was first characterized as proteinaceous on grounds of its inactivation by trypsin, attempts to purify and uniquely characterize were frustrated by its high specific activity as well as its apparent heterogeneity. Presently, some precision in determining molecular structure has been achieved for interferon. See P. B. Sehgal, supra; J. Collins, supra; and K. C. Zoon and R. Wetzel, supra.

In its earliest applications, interferon was employed exclusively as an antiviral agent and the most successful clinical therapeutic applications to date have been in the treatment of viral or virus-related disease states. It became apparent, however, that exogenous interferon was sometimes capable of effecting regression or remission of various metastatic diseases. An overview of current clinical trials of interferon as an antiviral and antiproliferative therapeutic agent through early 1983 is contained in The Biology of the Interferon System 1983, Proceedings of the Second International TNO Meeting on the Biology of the Interferon System, Rotterdam, The Netherlands, 18-22 April 1983, and Antiviral Research, March 1983, Special Abstract Issue, Elsevier/North-Holland Biomedical Press, Netherlands.

The clinical agent of choice in this work has been human leukocyte interferon, "mass-produced" by procedures involving collection and purification of vast quantities of human buffy coat leukocytes, induction with virus, and isolation from culture media. The need for interferon of human source is, of course, consistent with the longstanding conclusion that interferon is "species specific", i.e., biologically active, in vivo, only in species homologous to the source cells.

In the work described above, interferon has been administered parenterally, i.e., intramuscularly and intradermally, with some successful topical and intranasal usages having been reported. It has seldom been administered intravenously because of substantial adverse effects attributable to "contaminants" in crude and even highly purified isolates. The invention of applicant described in U.S. Pat. No. 4,462,985, and in PCT International Application No. PCT/US 81/01103, filed Aug. 18, 1981, published Mar. 4, 1982, concerns the use of interferon of heterologous species origin, and also involves oral administration of interferon. Prior to these disclosures, there had been no reports of therapeutically successful oral administration of interferon. This circumstance was consistent with the widely held belief that interferon would not withstand exposure to a digestive environment such as that found in mammals.

In addition to use in antiviral and antitumor therapy, interferon has rather recently been noted to possess immunomodulatory effects, both immunopotentiating and immunosuppressive in nature. B. Lebleu and J. Content, Mechanisms of Interferon Action: Biochemical and Genetic Approaches, Interferon 1982, Ed: I. Gresser, Academic Press, 1982, pp. 47-94; M. Moore, Interferon and the Immune System, 2: Effect of IFN on the Immune System, Interferons: From Molecular Biology to Clinical Application, Eds: D. C. Burke and A. G. Morris, Cambridge Univ. Press, 1983, pp. 181-209; H. Smith-Johannsen, Y-T Hou, X-T Liu, and Y-H Tan, Chapter 6, Regulatory Control of Interferon Synthesis and Action, Interferons and Their Applications, Eds: P. E. Came and W. A. Carter, Springer Verlag, (Handbook of Experimental Pharmacology V. 71) 1984, pp. 101-135; J. L. Raylor, J. L. Sabram, and S. E. Grossberg, Chapter 9, The Cellular Effects of Interferon, Ibid, pp. 169-204; J. M. Zarling, Effects of Interferon and Its Inducers on Leukocytes and Their Immunologic Functions, Ibid. pp. 403-431; R. Ravel, The Interferon System in Man: Nature of the Interferon Molecules and Mode of Action, Antiviral Drugs and Interferon: The Molecular Basics of Their Activity, Ed: Y. Becker, Martinus Nijhoff Pub., 1984, pp. 357-433.

Further, "new" biological activities for exogenous and endogenous interferon are consistently being ascertained. K. Berg, M. Hokland, and I. Heron, Biological Activities of Pure HuIFN-Alpha Species, Interferon, Properties, Mode of Action, Production, Clinical Application, Eds: K. Munk and H. Kirchner, (Beitrage zur Onkologie V. 11) pp. 118-126; S. Pestka et al, The Specific Molecular Activities of Interferons Differ for Antiviral, Antiproliferative and Natural Killer Cell Activities, The Biology of the Interferon System, 1983, Eds: E. DeMaeyer and H. Schellekens, pp. 535-549; P. K. Weck and P. E. Cane, Chapter 16, Comparative Biologic Activities of Human Interferons, Interferons and Their Applications, Eds: P. E. Came and W. A. Carter, Springer Verlag, (Handbook of Experimental Pharmacology V. 71) 1984, pp. 339-355.

One infectious disease which has not been controlled, by interferon or other means, is bovine respiratory disease complex (BRDC). BRDC is an all-encampassing term describing an acute, contagious infection of cattle characterized by inflammation of the upper respiratory passages and trachea. BRDC leads to pneumonia with clinical signs of dyspnea, anorexia, fever, depression, mucopurlent nasal discharge and mucopurulent ocular discharge, all of which result in high morbidity and mortality. BRDC is a major cause of disease loss in beef cattle. The economic loss to cattlemen for treatment, weight loss, death loss, and culling is estimated to be $333,000,000 annually (National Cattlemen's Association, 1980).

When BRDC symptomology is observed in cattle after transport to feedlots or pastures, it is commonly called "shipping fever." On their way to the feedlot, calves are subjected to the stresses of intensive management techniques, transportation without food or water, and a variety of infectious agents. Upon arrival at the feedlot, processing exposes the calves to the additional stresses of weaning, castration, dehorning, branding, eartagging, worming, vaccination, and delousing. In many situations, calves are stressed still further by changes in diet and environmental factors.

The infectious agents to which calves entering the marketing system are exposed include viruses (infectious bovine rhinotracheitis (IBR), non-IBR herpesviruses, parainfluenza type 3 (PI3), bovine viral diarrhea (BVD), respiratory syncytial, adenoviruses, enteroviruses, rhinoviruses, parvoviruses, and reoviruses), bacteria (*Pasteurella hemolytica, Pasteurella multocida,* and *Hemophilus somnus*), mycoplasma (*M. dispar, M. bovirhinis, M. bovis,* and *M. arginini*), and Chlamydia.

The IBR, BVD, and PI3 viruses are three of the infectious agents that are most commonly isolated by veterinary diagnostic laboratories in cases of BRDC. While some commercial vaccines for IBR, BVD, and PI3 are available, they have not been completely satisfactory in the past, partly because vaccination of calves stressed by shipping can exacerbate the clinical signs of the disease. Also, some calves will not develop antibodies after vaccination, leaving them still susceptible to infection. Furthermore, many commercial vaccines are designed to provide protection no sooner than 14 days after vaccination, tracking the U.S. Department of Agriculture, Bureau of Biologics, immunogenicity test. Because of the imperfections of the vaccination treatments used in the past and the enormous economic losses involved, a need exists for improved methods of preventing and treating bovine respiratory disease.

In a more general sense, a need exists for improved methods of vaccinating cattle and other warm-blooded vertebrates. Present vaccines are sometimes harmful. For example, they can produce a detrimental vaccine infection. If the efficiency of vaccines could be improved, then the amount of killed or attenuated microorganisms needed to give an effective vaccination dose could possibly be reduced. This would in turn descrease the chances of a detrimental vaccine infection and reduce the cost of the vaccine. The possibility of producing a quicker antibody response to vaccination would also exist.

Applicant has made the surprising discovery that administration of a biologically active interferon in conjunction with the administration of a vaccine can enhance the vaccine's efficiency.

SUMMARY OF THE INVENTION

A method in accordance with the present invention of enhancing the efficiency of a vaccine in warm-blooded vertebrates includes or comprises administering to a warm-blooded vertebrate, in conjunction with the administration of a vaccine, a biologically active interferon in a dosage no greater than about 5 IU/lb of body weight per day. The presently preferred dosage is about 1.0 IU of human interferon alpha per pound of body weight per day.

The interferon can be administered to the animal through a number of routes, such as orally, intranasally, intramuscularly, or intravenously. Oral administration is presently preferred. It can be administered in a single dose, either simultaneously with the administration of the vaccine or within about one day before or after the vaccine administration. Alternatively, the interferon can be administered in several doses, for example, by administering a dose on two or more of the days in the period consisting of the day before vaccine administration, the day of vaccine administration, and the day after vaccine administration. If the interferon and vaccine are administered simultaneously, they can be administered separately or mixed together.

The advantages of the present invention include enhanced vaccine efficiency by promotion of antibody production, earlier antibody production, and reduced vaccine costs as a result of using a smaller amount of microorganisms to product an effective dose. As an example of the latter advantage, current IBR vaccine dosages are about $10^{5.5}$ to $10^{6.0}$ TCD$_{50}$/ml. Applicant believes that the present invention should allow reduction of this dosage by a factor of about ten to one hundred.

The present invention achieves its effects with low doses of interferon. In addition to the favorable biological activity, using small doses naturally makes these methods less expensive than if they used large doses. Methods in accordance with the present invention are applicable to animal species such as bovine, porcine, caprine, ovine, avian, feline, canine, and equine species, as well as humans.

The interferon administered can be of heterologous or homologous species origin. ("Heterologous species origin" means that the interferon has been derived from cells of a species other than that to which it is administered.)

The optimum dosage of interferon varies somewhat species to species, and probably animal to animal. Also, effects similar to those produced by a given daily dosage administered for a given number of days might be achieved by administering a slightly lower dosage for a slightly greater number of days, or a slightly higher dosage for a slightly smaller number of days. Along the same lines, if an animal has an infection that is causing it to secrete some interferon naturally, the dosage to be administered might be reduced somewhat to achieve the same biological effects.

DETAILED DESCRIPTION OF SPECIFIC EMBODIMENTS

Applicant has filed several previous patent applications relating to methods or using interferon (U.S. Pat. Nos. 4,462,985 and 4,497,795, and U.S. patent application Ser. No. 688,868, filed on Jan. 4, 1985). They are incorporated in this specification by reference.

The methods of the present invention can use interferons produced by methods known to those skilled in the art. One specific suitable method of preparing an interferon is described below in Example 1. Examples 2-6 illustrate methods of using interferon. All geometric mean titers of antibody are expressed to the base 2 in the following examples.

EXAMPLE 1

Human interferon alpha can be prepared throught the following procedure, commonly referred to as the Cantell procedure. The process begins with packs of human leukocytes, obtained in this case from the Gulf Coast Regional Blood Center, Houston, Texas. The buffy coats in these packs are pooled into centrifuge bottles, and then are diluted with 0.83% ammonium chloride. The mixture is incubated for 15 minutes with intermittent shaking, and is then centrifuged for 20 minutes at 2000 rpm. The supernatant is discarded, and the cell pellets are resuspended with a minimal volume of sterile phosphate buffered saline (PBS). The mixture is then diluted with ammonium chloride and centrifuged. The supernatant is again discarded, and the remaining cell pellets are resuspended with a minimal volume of a tissue culture medium such as Minimal Essential Medium (MEM), available from KC Biological. The cell concentration is determined with a Coulter counter.

Interferon induction takes place in glass or plastic bottles. The induction medium contains MEM, 75 mM Hepes (available from Calbiochem), 75 mM Tricine (available from Sigma Chemical Co.), human agamma serum (18 mg/ml), and gentamycin sulfate (from M. A. Bioproducts; 50 mcg/ml). The cells are added to the induction vessels at a final concentration of about 5 to 10 million cells per milliliter. The induction vessel is incubated in a 37° C. water bath, and interferon alpha is added as a primer.

After two hours, Sendai virus is added to the induction mixture. This causes, alpha interferon to be produced in the supernatant by the leukocytes. After a 12-18 hour incubation time, the induction mixture is centrifuged. The cells are discarded, and the supernatant is then purified.

The crude interferon is chilled to 10° C. or below in an ice bath. Five molar potassium thiocyanate is added to obtain a final concentration of 0.5M. This solution is stirred for 15 minutes, and then its pH is lowered to 3.3 by adding hydrochloric acid. The mixture is then centrifuged at 2800 rpm for 30 minutes, and the supernatant is discarded.

The pellets are then resuspended in 95% ethanol and are stirred for 15 minutes. This suspension is centrifuged at 2800 rpm for 20 minutes, and the pellets are discarded. The pH of the supernatant is then adjusted to 5.8 with sodium hydroxide. The mixture is stirred for 10 minutes, and then centrifuged at 2800 rpm for 20 minutes. The pellets are discarded. The pH of the supernatant is then adjusted to 8 with sodium hydroxide. This solution is stirred for 10 minutes, followed by centrifugation at 2800 rpm for 20 minutes. The supernatant is discarded, and the pellets are resuspended with 0.5M potassium thiocyanate in a 0.1M sodium phosphate buffer. This suspension is stirred at 4° 1 C.

Next, the suspension is centrifuged at 2800 rpm for 20 minutes, and the pellets are discarded. The pH of the supernatant is adjusted to 5.3 with hydrochloric acid.

After stirring for 10 minutes and centrifugation, the pH of the supernatant is adjusted to 2.8 with hydrochloric acid, followed by further stirring for 20 minutes. This mixture is centrifuged at 2800 rpm, and the resulting pellet is purified human interferon alpha.

The pellet is resuspended with 0.5M potassium thiocyanate in 0.1M sodium phosphate buffer, having a pH of 8.0. It is then dialyzed against PBS at 4° C., with two changes of PBS. This mixture is then centrifuged and the precipitate is discarded. The remaining purified alpha interferon is sterilized by filtration through a 0.2 micron filter.

A human interferon alpha is produced in accordance with this procedure by Immuno Modulators Laboratories, Inc., Stafford, Texas, and sold under the trademark Agriferon®-C for use in cattle.

Other procedures known to those skilled in the art are available for making interferons, such as human interferon alpha and human inteferon gamma. For example, U.S. Pat. Nos. 4,376,821 and 4,460,685 disclose methods of making human interferon gamma. A method of making bovine fibroblast interferon is disclosed in applicant's U.S. Pat. No. 4,462,985.

EXAMPLE 2

Forty feeder calves were randomly assigned to four treatment groups of ten calves each. All of the calves were initially seronegative to IBR virus. The calves were given either a placebo or human interferon alpha orally in three consecutive daily dosages of 0.05, 0.5, or 5.0 IU/lb body weight, respectively. A dose of interferon or the placebo was given on the day before, the day after, and the day of IBR virus inoculation. Each calf was given $10^3$ plaque forming units (PFU) of IBR virus per nostril.

Tables 1–3 show the results of this test.

As Table 1 shows, the rectal temperatures of the cattle differ significantly among the four treatment groups after inoculation. More calves given the 0.5 IU/lb dosage than controls had a fever of at least 104° F. at 5, 6, 7, 8 and 9 days after inoculation. More control calves had a fever greater than 104° F. at 14 and 18 days after virus inoculation.

Antibodies to IBR virus were produced in all groups. However, Table 2 shows that antibody production occurred significantly faster in the group treated with 0.5 IU/lb. Nasal excretion of IBR virus also occurred and disappeared sooner in the 0.5 IU/lb treatment group, as shown in Table 3. Significantly more virus was excreted by the 0.5 IU/lb treatment group than by controls at 3 and 7 days after IBR virus inoculation, but significantly less virus was excreted at 14 days after inoculation. At 14 days, only 7 PFU of virus were excreted by calves given 0.5 IU/lb compared to over 12,000 PFU of virus excretion from controls.

In summary, human interferon alpha administered orally at 0.5 IU/lb of body weight significantly stimulated antibody development at 14 days after IBR virus inoculation and significantly reduced IBR virus shedding at 14 days after inoculation.

EXAMPLE 3

A number of light weight feeder calves (average weight 460 lbs) were shipped to a feedlot, and subsequently many experienced a natural shipping fever outbreak. The calves were not vaccinated. The calves were tested for the presence of anitbody to PI3 virus. The calves that tested seronegative were divided into three treatment groups, and human interferon alpha or placebo was administered to the three groups in three consecutive daily oral doses of 0, 0.1, or 1.0 IU/lb of body weight, respectively. Table 4 shows the results of this test.

TABLE 1

| Treatment Group | Number of Calves with a Temperature of at Least 104° F. Days After IBR Virus Inoculation | | | | | | | | | | | | | | |
|---|---|---|---|---|---|---|---|---|---|---|---|---|---|---|---|
| | −1 | 0 | 1 | 2–4 | 5 | 6 | 7 | 8 | 9 | 10 | 14 | 18 | 19 | 23 | 25 | Total |
| Control | 1 | 0 | 2 | 1 | 0 | 1 | 1 | 2 | 0 | 0 | 3 | 4 | 1 | 2 | 0 | 18 |
| 0.05 IU/lb | 1 | 1 | 1 | 0 | 2 | 3 | 4 | 4 | 3 | 4 | 2 | 2 | 0 | 2 | 0 | 29 |
| 0.5 IU/lb | 0 | 0 | 1 | 0 | 2 | 5 | 7 | 6 | 3 | 1 | 0 | 0 | 0 | 0 | 0 | 25 |
| 5.0 IU/lb | 1 | 1 | 1 | 1 | 3 | 2 | 6 | 4 | 1 | 0 | 1 | 2 | 0 | 2 | 0 | 25 |

TABLE 2

Geometric Mean Serum Antibody Titers to IBR Virus

| Treatment Group | Days After Virus | | |
|---|---|---|---|
| | 0 | 14 | 25 |
| Control | 0 | 1.9 | 29.8 |
| 0.05 IU/lb | 0 | 3.7 | 27.9 |
| 0.5 IU/lb | 0 | 8.8 | 24.3 |
| 5.0 IU/lb | 0 | 4.6 | 21.1 |

TABLE 3

Geoetric Mean Titers of Plaque Forming Units (PFU) of IBR Virus Excretion

| Treatment Group | Days after Inoculation | | | | |
|---|---|---|---|---|---|
| | 0 | 3 | 7 | 10 | 14 |
| Control | 0 | 2 | 204 | 6,310 | 12,078 |
| 0.05 IU/lb | 0 | 21 | 3,396 | 174,582 | 298 |
| 0.5 IU/lb | 0 | 221 | 20,749 | 20,184 | 7 |
| 5.0 IU/lb | 0 | 71 | 4,130 | 43,451 | 132 |

TABLE 4

Serology to Parainfluenza-3 Virus 28 Days after Arrival at Feedlot

| No. of Seronegative Calves | Treatment Group (IU/lb body wt.) | Seroconversion at 28 Days |
|---|---|---|
| 31 | 0.00 | 71% |
| 30 | 0.10 | 96% |
| 33 | 1.00 | 75% |

As Table 4 shows, the calves treated with the 0.1 IU/lb dose achieved significantly better seroconversion to PI3 virus during natural disease than calves treated with 1.0 IU/lb or with placebo.

EXAMPLE 4

A number of calves were divided into six treatment groups of eighteen each. Two of the treatment groups were given a full dose of vaccine, two groups were given a hundred fold reduced dose of vaccine, and the remaining two groups were not vaccinated. For each of the pairs of treatment groups, one group was treated orally with interferon and one was not.

The vaccine was an IBR-PI3-BVD modified live virus vaccine obtained from CEVA Labs, serial no. 71020L39, and contained at least $10^{5.7}$ TCD$_{50}$/ml of IBR virus, $10^{4.3}$ TCD$_{50}$/ml of BVD virus, and $10^{4.7}$ TCD$_{50}$/ml of PI3 virus. The vacinnation was administered intramuscularly. The interferon treatment was a single oral dose of human interferon alpha at the rate of 1.0 IU/lb of body weight and was administered at the time of vaccination. Tables 5-7 show the results of this test.

TABLE 5

Geometric Mean Antibody Titers to IBR Virus 13 and 25 Days after Vaccination of Seronegative Calves

| Vaccine Dose | Treatment | No. of Calves | GMT after Vaccination on Day 13 | 25 |
|---|---|---|---|---|
| 1:100× | Placebo | 14 | 1.8 | 5.7 |
| 1:100× | Interferon | 15 | 2.3 | 4.2 |
| 1× | Placebo | 15 | 2.9 | 5.3 |
| 1× | Interferon | 16 | 3.0 | 7.3 |

TABLE 6

Geometric Mean Antibody Titers to BVD Virus 13 and 25 Days after Vaccination of Seronecative Calves

| Vaccine Dose | Treatment | No. of Calves | GMT after Vaccination on Day 13 | 25 |
|---|---|---|---|---|
| 1:100× | Placebo | 15 | 1.3 | 5.5 |
| 1:100× | Interferon | 11 | 1.4 | 3.1 |
| 1× | Placebo | 14 | 1.3 | 11.2 |
| 1× | Interferon | 15 | 2.4 | 12.7 |

TABLE 7

Seroconversion to PI3 Virus 0 and 25 Days after Inoculation with a Full Dose of Vaccine

| Calf | Treatment | PI3 Virus Antibody Titer on Day 0 | 25 |
|---|---|---|---|
| A | Placebo | <4 | <4 |
| B | Placebo | <4 | <4 |
| C | Interferon | <4 | 16 |
| D | Interferon | <4 | 8 |
| E | Interferon | <4 | 4 |
| F | Interferon | <4 | 8 |
| G | Interferon | <4 | 4 |

Table 5 shows that calves treated with interferon produced slightly higher geometric mean titers to IBR virus at 13 days after vaccination than did calves not treated with interferon at equal vaccine dosages. Table 6 shows that the same was generally true for geometric mean antibody titer to BVD virus. Table 7 shows a significant improvement in seroconversion in calves treated with interferon versus controls. Neither of the two calves (A and B) reported in this table who were not treated with interferon achieved a PI3 virus antibody titer of as high as four on the 25th day after vaccination. However, each of the five calves (C-G) treated with interferon had achieved a titer of at least four by that time.

EXAMPLE 5

One hundred calves were divided into five treatment groups of twenty each. One group was used as controls and was vaccinated but not treated with interferon. The other four groups were vaccinated and treated with either one dose of lyophilized interferon, two doses of lyophilized interferon, one dose of interferon that had been frozen, or two doses of interferon that had been frozen. The interferon was human interferon alpha and each oral dose was 1.0 IU/lb of body weight. The vaccination was with the same vaccine identified in Example 4. Tables 8-10 show the results of this test.

TABLE 8

Geometric Mean Titers of Antibody of Seronegative Calves to IBR Virus 14 Days after Vaccination

| | | 14 Days after Vaccination | |
|---|---|---|---|
| Treatment | No. of Calves | No. of Calves With Titer >8 | GMT |
| Control | 16 | 7 | 4.2 |
| lyo. once | 18 | 8 | 4.0 |
| lyo. twice | 18 | 11 | 5.0 |

TABLE 9

Geometric Mean Titers of Antibody of Seronegative Calves to BVD Virus 28 Days After Vaccination

| Treatment | No. of Calves | GMT |
|---|---|---|
| Control | 15 | 12.7 |
| lyo. once | 17 | 14.7 |
| lyo. twice | 12 | 13.5 |
| froz. once | 19 | 19.2 |
| froz. twice | 16 | 15.3 |

TABLE 10

| | | Fever and Sickness | | |
|---|---|---|---|---|
| | | Fever | | Antibiotic |
| No. of Calves | Treatment | Peak (°F.) | Duration ≧104° F. | Treatment Days |
| 16 | Control | 105.4 | 2.88 | 6.4 |
| 18 | lyo. once | 105.5 | 2.28 | 5.8 |
| 17 | lyo. twice | 105.5 | 2.35 | 5.9 |
| 16 | froz. once | 105.1 | 2.31 | 5.6 |
| 18 | froz. twice | 105.3 | 3.11 | 6.7 |

Table 8 shows that a slightly higher percentage of calves achieved a geometric mean antibody titer to IBR virus of at least eight by the fourteenth day after vaccination if they had been treated with interferon. Table 9 shows that all interferon treatment groups produced higher GMT's of antibody to BVD virus at 28 days than did the controls. Table 10 shows that the most groups of calves treated with interferon had a shorter fever duration.

EXAMPLE 6

One hundred two light weight feeder steers and bulls (average pay weight 442 lbs.) were purchased from an order buyer in Tennessee. The calves were trucked to Texas and then treated with nothing or human interferon alpha orally (1 IU/lb) on arrival. The next day during processing the calves were given another 1 IU/lb dose of interferon and were vaccinated as shown in Table 11.

TABLE 11

| No. of Calves | Interferon | BVD Vaccine |
|---|---|---|
| 17 | twice | none |
| 17 | none | none |
| 17 | twice | Diamond Labs (killed) |
| 17 | none | Diamond Labs (killed) |
| 17 | twice | Nordens MLV TS (Lot A/3.18.85) |
| 17 | none | Nordens MLV TS (Lot A/3.18.85) |

Tables 12-15 show the results of this test.

TABLE 12

Number of Calves Treated With Antibiotics Because Fever ≧104° F.

| Treatment | | No. of Calves Treated On | | | |
|---|---|---|---|---|---|
| BVD Vaccine | Interferon | Arrival | Processing | +1 Day | Later |
| none | none | 2 | 12 | 2 | 0 |
| none | twice | 3 | 8 | 2 | 2 |
| killed | none | 2 | 8 | 1 | 2 |
| killed | twice | 2 | 8 | 6 | 1 |
| live | none | 2 | 10 | 1 | 3 |
| live | twice | 5 | 8 | 1 | 1 |

TABLE 13

Morbidity and Retreatment Rates

| Treatment | | Morbidity | Retreatment |
|---|---|---|---|
| BVD Vaccine | Interferon | Rate(%) | Rate(%) |
| none | none | 93 | 79 |
| none | twice | 86 | 50 |
| killed | none | 73 | 36 |
| killed | twice | 100 | 53 |
| live | none | 83 | 50 |
| live | twice | 93 | 90 |

TABLE 14

Fever Duration and Peak Temperature

| No. of Calves | Treatment | | Fever(Avg.) | |
|---|---|---|---|---|
| | BVD Vaccine | Interferon | Duration* | Peak(°F.) |
| 16 | none | none | 2.1 | 105.5 |
| 15 | none | twice | 2.4 | 105.1 |
| 13 | killed | none | 2.4 | 105.3 |
| 17 | killed | twice | 1.9 | 105.2 |
| 16 | live | none | 2.2 | 105.3 |
| 15 | live | twice | 3.1 | 105.8 |

*Duration in days with fever ≧104° F.

TABLE 15

Serological Response

| No. of Calves | Treatment | No. of Seroconversions | GMT of BVD Antibody 28 Days After Vaccination |
|---|---|---|---|
| 15 | BVD vaccine + interferon | 11 | 6.65 |
| 16 | BVD vaccine only | 6 | 3.22 |

Table 12 shows the number of calves in each group that were treated with antibiotics because of having a fever of at least 104° F. The number is given for the day of arrival, the day of processing, one day after processing, and finally several days after processing. As the "arrival" column shows, substantially more calves in the group that was vaccinated with live virus and given two doses of interferon were sick before the vaccination. This is probably also reflected to some extent in the results shown in the subsequent tables.

Table 13 shows the percentage morbidity rate, that is, the percentage of calves that required antibiotics treatment, and the percentage of calves that required retreatment with antibiotics. Table 14 shows the fever experienced by the calves in the different groups. In the groups vaccinated with live virus, the duration of fever over 104° F. was treated in calves treated with interferon. Table 15 shows that seroconversion and GMT of BVD antibody were significantly improved in calves treated with interferon.

If interferon is to be administered to animals simultaneously with the administration of a vaccine, the two can be administered separately or mixed together. ("Simultaneously" is used here and in the claims to mean administration within a few minutes of the same time, not necessarily at the same precise second.) If they are mixed together, the formulation can be the same as standard vaccine formulations (which include a suspension of attenuated or killed microorganisms suitable for inducing immunity to an infectious disease). Such vaccine formulations are well known to those skilled in the art. The only change would be the addition of the necessary amount of a biologically active interferon. Such formulations can include pharmaceutically acceptable carriers such as phosphate buffered saline (PBS).

The preceeding specification describes specific embodiments of this invention for the purposes of illustration and explanation. Those skilled in this art will recognize that many modifications could be made to the materials and methods described that would still be within the scope and spirit of the invention. Applicant intends for the following claims to be interpreted to include all such modifications.

What is claimed is:

1. In a method of enhancing the efficiency of a vaccine in a warm blooded vertebrate by administering to said vertebrate, in conjunction with the administration of a vaccine, a biologically active interferon, the improvement which comprises administering interferon orally to said vertebrate in a dosage no greater than 5 IU/lb of body weight per day.

2. The improvement of claim 1 where the dosage is about 1.0 IU/lb of body weight per day.

3. The improvement of claim 1, where the interferon is administered simultaneously with the vaccine.

4. The improvement of claim 1, where the interferon is administered within about one day before or after the time when the vaccine is administered.

5. The improvement of claim 1, where the interferon is administered on two or more of the days in the period consisting of the day before vaccine administration, the day of vaccine administration, and the day after vaccine administration.

6. The improvement of claim 1, where the interferon is human interferon alpha.

7. The improvement of claim 1, where the dosage is about 1.0 IU/lb of body weight per day, the interferon is human interferon alpha, and is administrated orally simultaneously with the vaccine.

* * * * *